United States Patent [19]
Brooks

[11] Patent Number: 6,053,860
[45] Date of Patent: Apr. 25, 2000

[54] APPARATUS FOR VIEWING AND TREATING BODY TISSUE

[75] Inventor: Albert E. Brooks, Ventura, Calif.

[73] Assignee: Andco Tek Inc., Ventura, Calif.

[21] Appl. No.: 08/926,085

[22] Filed: Sep. 2, 1997

[51] Int. Cl.$^7$ ..................................................... A61B 1/06
[52] U.S. Cl. .......................... 600/137; 600/104; 600/106; 600/153
[58] Field of Search ................... 600/104, 105, 600/106, 121, 123, 127, 135, 137, 153, 156

[56] References Cited

U.S. PATENT DOCUMENTS

| | | | |
|---|---|---|---|
| 4,762,120 | 8/1988 | Hussein | 600/137 |
| 5,088,819 | 2/1992 | Storz | 600/137 |
| 5,188,093 | 2/1993 | Lafferty | 600/137 |
| 5,359,991 | 11/1994 | Takahashi | 600/123 |
| 5,464,404 | 11/1995 | Abela | 606/41 |
| 5,486,155 | 1/1996 | Muller | 600/137 |
| 5,577,654 | 11/1996 | Bishop | 600/137 |
| 5,582,575 | 12/1996 | Heckele | 600/137 |
| 5,702,344 | 12/1997 | Silverstein | 600/123 |

*Primary Examiner*—John P. Leubecker
*Assistant Examiner*—Ira Hatton
*Attorney, Agent, or Firm*—William W. Haefliger

[57] ABSTRACT

In the method of treating internal body tissue, the steps that include providing an endoscope having a viewing channel, with an elongated optical stem, associated with the channel, and defining a longitudinal axis; providing a longitudinally elongated sheath received on a stem and supported for controlled rotation about an axis and into selected angular position relative to a support, to gain access to the selected urethral tissue zone to be treated; providing means to be rotated with the sheath to be targeted toward and to eject flowable treatment material onto or into tissue at a zone; and rotating the sheath and ejecting treatment material at a selected zone.

20 Claims, 5 Drawing Sheets

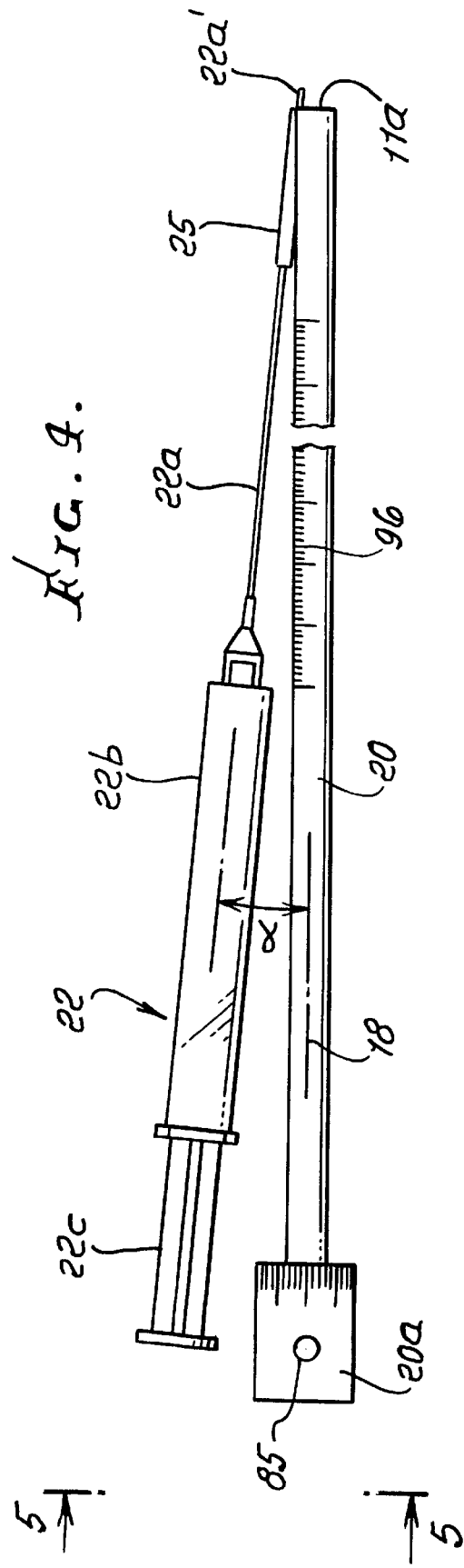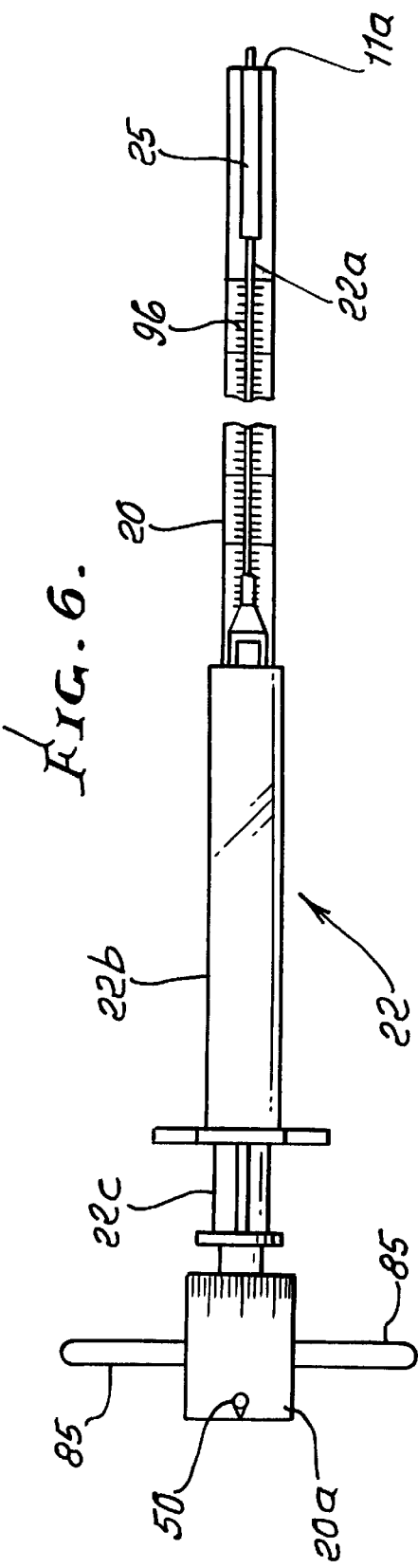

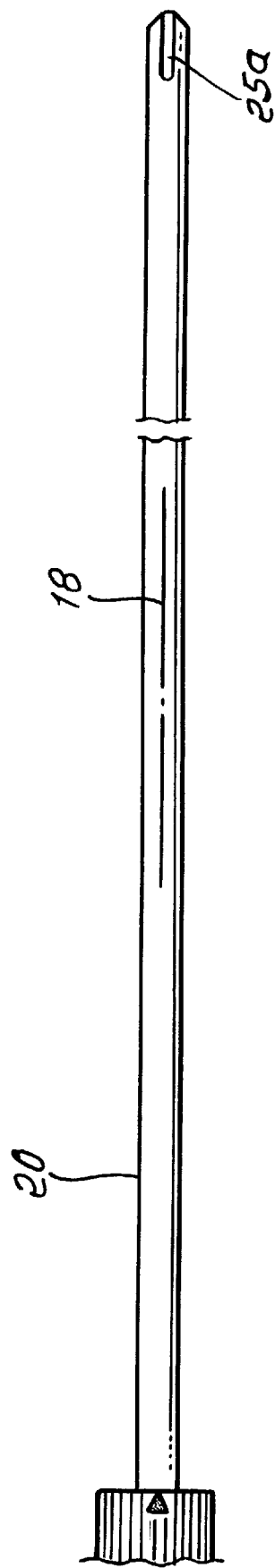
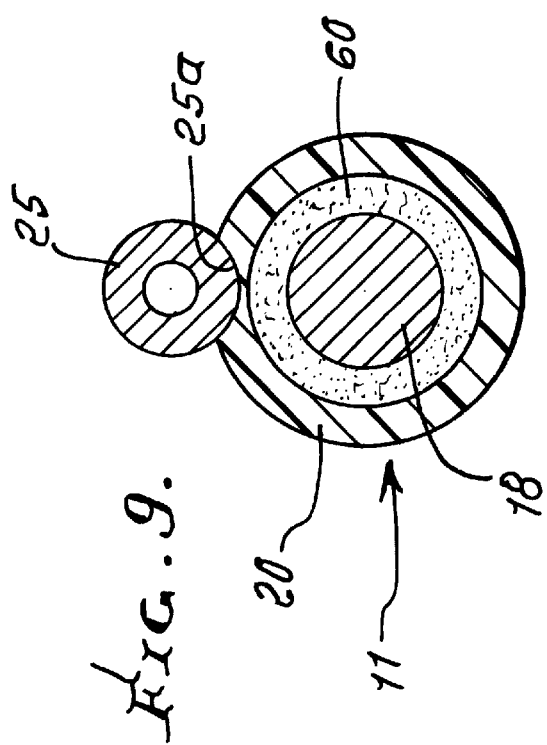

APPARATUS FOR VIEWING AND TREATING BODY TISSUE

BACKGROUND OF THE INVENTION

This invention relates generally to the treatment of intraurethral body tissue, and more particularly to the method and apparatus for accurately injecting flowable treatment material into the intraurethral body tissue.

There is great need for improved method and apparatus to accomplish such accurate injection of flowable treatment material, as for example, but not limited to urethral tissue zones.

SUMMARY OF THE INVENTION

It is a major object of the invention to provide method and apparatus to meet the above need. Basically, the method of treating internal body tissue, in accordance with the invention, comprises:

a) providing an endoscope having a viewing channel, with an elongated optical stem, associated with said channel, and defining a longitudinal axis, b) providing a longitudinally elongated sheath received on said stem and supported for controlled rotation about said axis and into selected angular position relative to said support, to gain access to the selected urethral tissue zone to be treated, c) and providing means operable through rotation of the sheath to be targeted toward and to eject flowable treatment material onto or into said tissue at said zone, d) and rotating said sheath and ejecting said treatment material at said selected zone.

The method is particularly useful for injecting collagen into a zone or zones proximate the human urethra, the sheath typically being inserted into the urethra for that purpose.

Another object comprises providing a syringe having a needle, providing a needle guide on said sheath in offset relation to the sheath axis, near forward end extent of the sheath, and inserting the syringe needle into a said guide on the sheath, so that the needle discharge end is proximate the end of the sheath. In this regard, provision is typically made for illuminating the zone to be treated, and when the sleeve is rotated; and for viewing that zone via the viewing channel.

Further objects are to provide indications of the extent of such rotating of said sheath, visible via the viewing channel; providing an eyepiece on the support in optical alignment with the viewing channel; providing a handle for the support and illumination means in the handle; providing a sheath bearing on the support; and providing sealing means between the sheath and bearing.

In accordance with a further object, apparatus is provided for performing the above described method, that apparatus comprising:

a) a support providing a viewing channel, and an elongated optical stem, associated with said channel, and defining an axis, b) a sheath received on said stem and supported for controlled rotation about said axis and into selected angular position relative to said support, to gain access to a selected body tissue zone to be treated, c) means carried on the sheath to be rotated therewith, to eject flowable treatment material onto or into tissue at said zone, d) the sheath being controllably rotatable to selected angular position about said axis to enable controlled ejection of the treatment material at the selected zone.

In this regard, the sheath advantageously carries an angular guide for a syringe needle, in offset relation to said axis, to inject said flowable material after rotation of the sheath to selected angular position; and means may be located on the sheath and on the support to provide indications of the extent of such rotating of said sheath, visible via the viewing channel.

These and other objects and advantages of the invention, as well as the details of an illustrative embodiment, will be more fully understood from the following specification and drawings, in which:

DRAWING DESCRIPTION

FIG. 4 is an elevation showing a preferred sheath and syringe support relationship;

FIG. 6 is a top plan view of the syringe and sheath of FIG. 4;

FIG. 8 is a top plan view of a support stem, to support the sheath for rotation; and FIG. 9 is an enlarged section taken crosswise of the stem and through a fiber optics zone.

DETAILED DESCRIPTION

Figure 1:
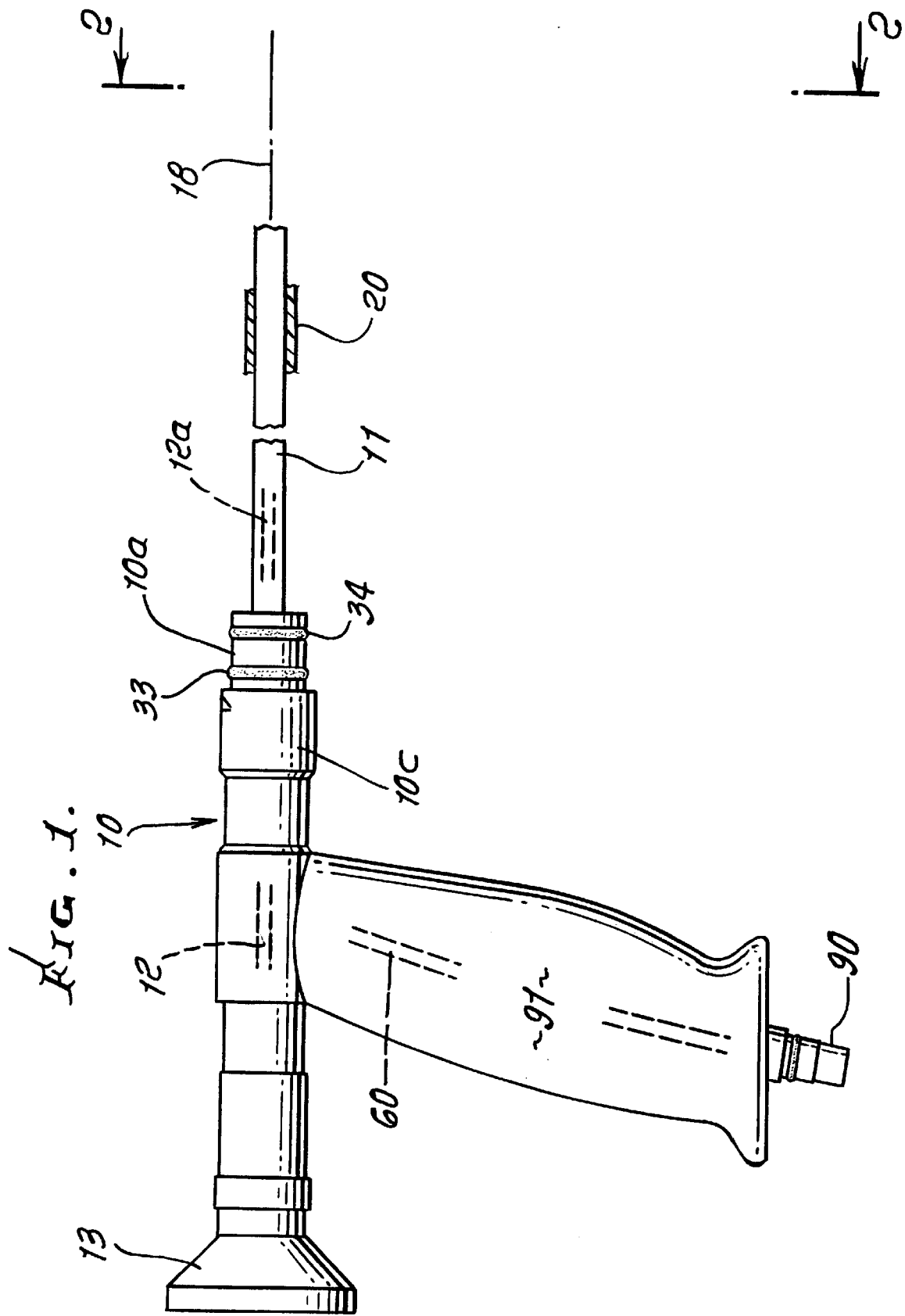
FIG. 1 is a side elevation showing apparatus incorporating the invention.

In the drawings, a support is provided, having a viewing channel, and an elongated support stem. See for example longitudinally elongated support body 10 in FIG. 1, having support stem 11 projecting longitudinally forwardly, along axis 18. Stem 11 may be integral with body 10. A viewing channel 12 is provided in body 10, in alignment with an eyepiece 13 carried by the body. A forward extension of the viewing channel is shown at 12a in the stem. Therefore, the viewing channel enables viewing of a selected body tissue zone to be treated, forwardly of the stem end 11a. That zone may be located in the urethra, into which the stem is inserted. It is schematically shown at 19.

A tubular sheath 20 is provided to be slidably received axially endwise on the tubular stem 11, for controlled rotation about axis 18, and into selected angular position relative to the support stem 11. Such rotation allows accurate access to be gained to a selected tissue zone to be treated, as represented for example at 19. Means such as a syringe 22 is provided to be carried or guided by or on the sheath, or otherwise associated with the sheath, to rotate with the sheath and thereby targeted toward the selected tissue zone and for ejecting flowable treatment material onto or into the tissue at the selected zone, for treating the tissue. One such flowable material is collagen, to be applied to a targeted urethral tissue zone, the stem 11 and sheath having been inserted into the urethra. The invention enables more accurate targeting of the tissue zone, by means of controlled rotation of the sheath about axis 18, and along with the syringe 22, and the syringe elongated stem or needle 22a, via the end of which the flowable treatment is ejected. In the preferred example shown, a needle guide 25, such as a small tube, is provided on the sheath in angularly offset relation to axis 18, and near the forwardmost end or end extent of the sheath. The needle 22a is inserted into the guide, which thereby enables the needle and syringe to be supported at an angle α relative to axis 18, for rotation with the sheath about axis 18, to accurately direct the needle end toward the precise portion of the tissue zone to be treated, as during viewing via the eyepiece for example. A syringe tube and plunger are seen at 22b and 22c. Needle end 22a' is shown in FIG. 4. Treatment material, as for example collagen, or other material, may thereby be accurately applied to a urethral zone to be treated. The small angle α (less than about 15°) further facilitates insertion of the forward ends of the sheath syringe needle into the urethral duct. A groove 25a in the sheath end periphery receives the guide 25, bonded in place. See FIG. 9.

Controlled rotation of the sheath about axis 18, and relative to stem 11 is enhanced by provision of an enlarged rearward tubular bearing portion 20a of the sheath which is easily grasped by the user. Note for example rotational adjustment assist bars 85 connected to 20a. Portion 20a has a bore 32 that fits over two coaxial elastomeric O-rings 33 and 34 on forward cylindrical extent 10a of the support 10. Those O-rings provide frictional engagement with bore 32 to provide some frictional resistance to sleeve rotation, and to frictionally position the bearing and the sleeve at a selected angular position of rotation about axis 18, which in turn accurately positions the angled and offset end of the syringe needle relative to the tissue zone to be treated. Dual O-rings provide a coaxial aligned support of the bearing and its bore, relative to axis 18.

Another function of the O-rings is to block leakage of fluid from between the support and the sleeve. Such fluid may for example be injected via a valve control 40 at the side of the support 10, and a duct 40a in the stem 11, to the stem rightward discharge end. Bladder treating liquid may be infused in this way, and some liquid may pass rearwardly between the stem 11 and sheath, to the bearing, where leakage is thereby prevented.

Illumination of the zone to be treated may be provided as by optical fibers 60 in an annular bundle extending between 20 and 18, and also extending between a light source 90 below handle 91, and the forward end of stem 11. See FIG. 9. Stem 11 may consist of transparent plastic material, for viewing, and the sheath 20 may consist of non-transparent plastic material.

Means is also provided on the sheath and on the support to enable visual indication of the extent of rotation of the sheath relative to the stem 11. See for example the marker 50 on the bearing or knob 20a, which successively aligns with the circularly arrayed gradations indicia as on the support portion 10c. Knob 20a extends endwise adjacent portion 10c, as seen in FIG. 3.

Provision may be made for optical viewing of rotation indicating indicia, and extent of sheath rotation, via the eyepiece.

Figure 2:
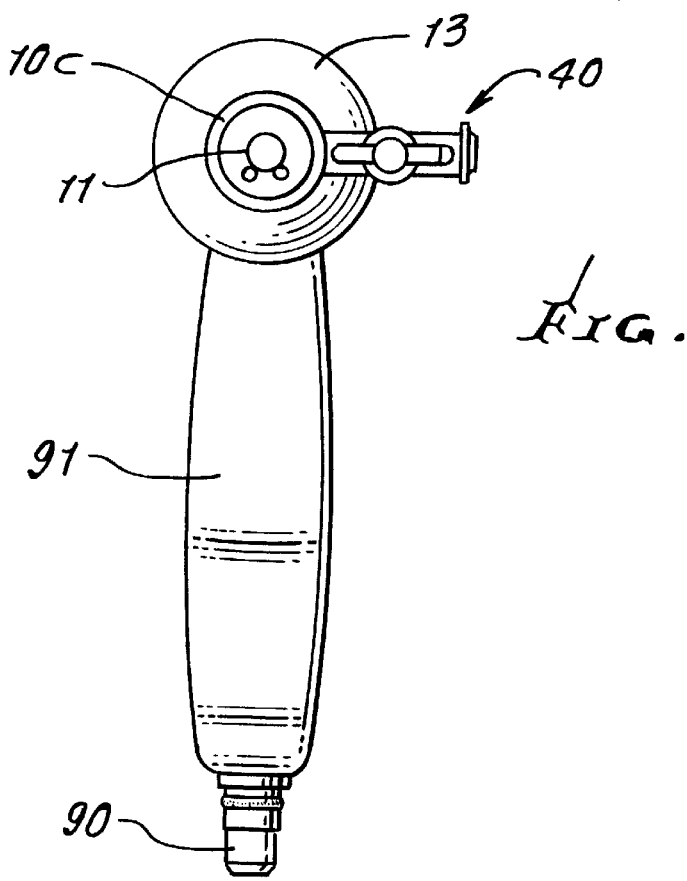
FIG. 2 is an end view taken on lines 2—2 of FIG. 1.
Figure 5:
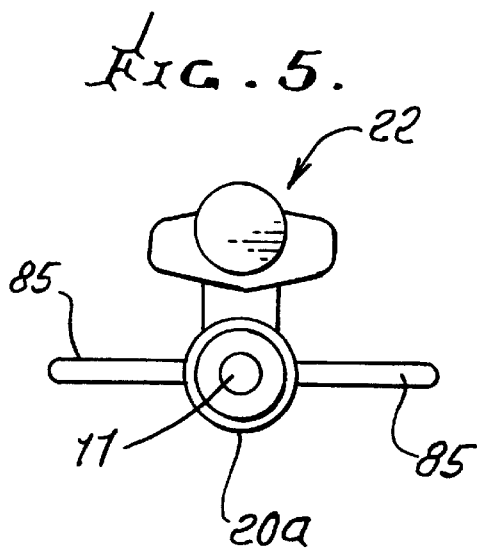
FIG. 5 is an end view taken on lines 5—5 of FIG. 4.
Figure 7:
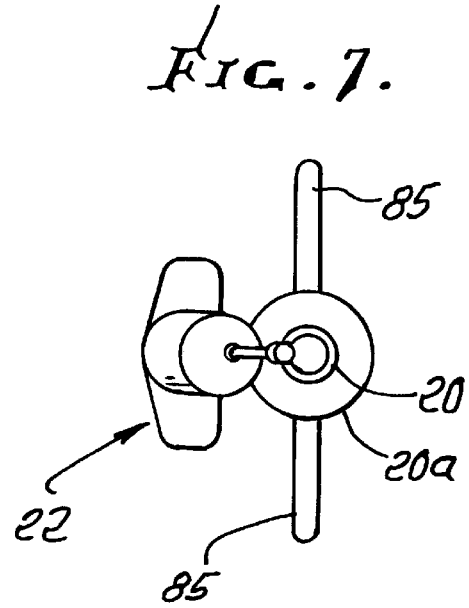
FIG. 7 is an end view taken on lines 7—7 of FIG. 6.
Figure 3:
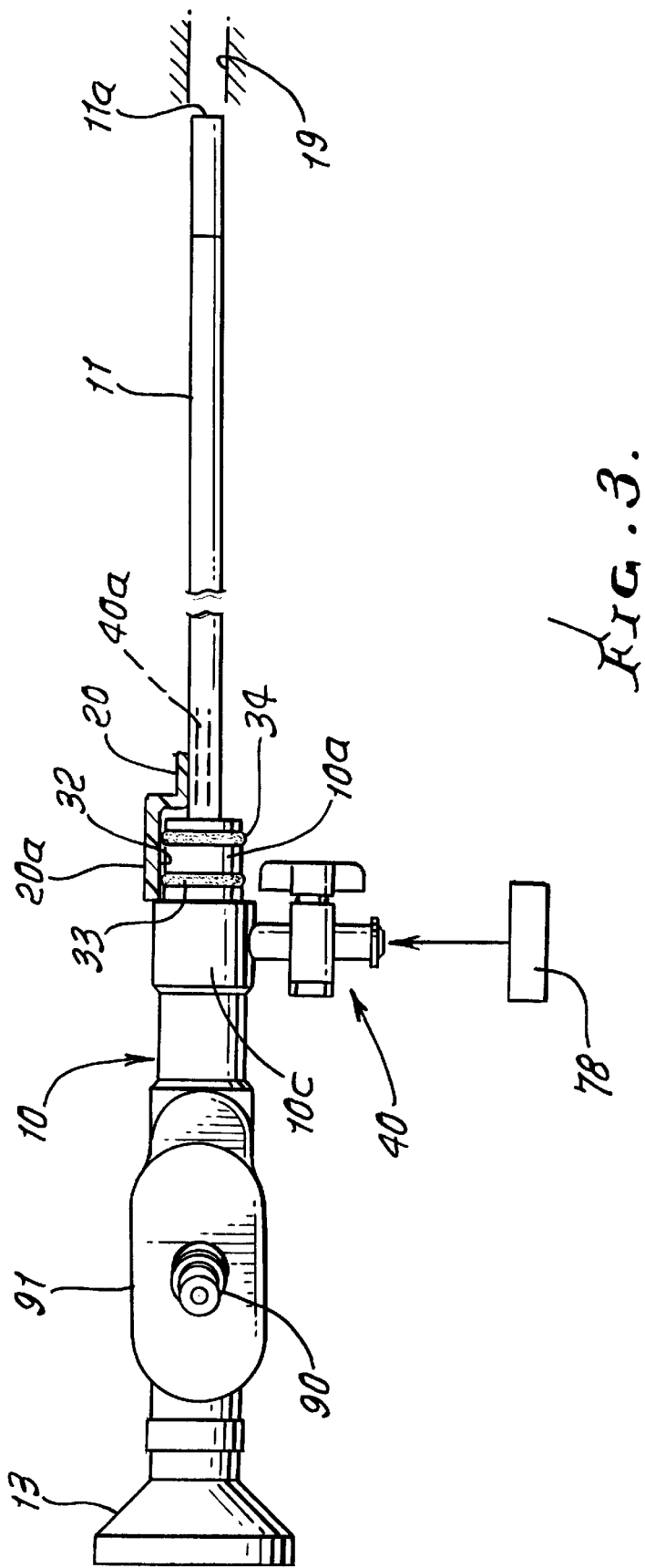
FIG. 3 is a bottom plan view of the FIG. 1 apparatus.

FIGS. 2, 3 and 9 show provision of means to infuse treatment liquid or gas into the body, as into the bladder, the syringe at that time being rearward. See in this regard duct 40a within the stem 11 and communicating between a liquid or gas source 78 and an outlet at the forward end of the stem. A valve control is provided at 40 between the source 78 and the stem, and at the side of support 10.

Indicia gradations 96 are provided on the sheath 20. The syringe plunger forward extent 22c' progressively registers with such indicia during injection, to provide an indication of the amount of flowable material being injected.

I claim:

1. In the method of treating internal body tissue, the steps that include
   a) providing an endoscope having a viewing channel, with an elongated optical stem, associated with said channel, and defining a longitudinal axis,
   b) providing a longitudinally elongated sheath received on said stem and supported for controlled rotation about said axis and into selected angular position relative to said support, to gain access to the selected urethral tissue zone to be treated,
   c) providing means to be rotated with the sheath, to be targeted toward and to eject flowable treatment material onto or into said tissue at said zone, said means provided in the form of a syringe having a needle, providing a needle guide on and exposed externally of said sheath in angularly offset relation to said axis, near forward end extent of the sheath, and inserting the syringe needle forwardly into a guide on the sheath, so that the needle discharge end is proximate the end of the sheath.

2. The method of claim 1 wherein said flowable material consists of collagen.

3. The method of claim 1 wherein said zone is proximate the urethra.

4. The method of claim 3 including inserting said sheath into the urethra.

5. The method of claim 1 including passing said treatment material adjacent at least a portion of said sheath angularly offset from said axis after rotation of the sheath to said selected angular position.

6. The method of claim 1 including providing indications of the extent of said rotating of said sheath, visible via said viewing channel.

7. The method of claim 5 including illuminating said zone while said sleeve is rotated.

8. The method of claim 7 including viewing said zone via said viewing channel and said stem.

9. The method of claim 5 including providing said means in the form of a syringe having a needle, providing a needle guide on said sheath in offset relation to said axis, near forward end extent of the sheath, and inserting the syringe needle into a said guide on the sheath, so that the needle discharge end is proximate the end of the sheath.

10. The method of claim 1 including providing an eyepiece carried on said support, in optical alignment with said viewing channel.

11. The method of claim 1 including providing a hand grip on which said support is mounted.

12. The method of claim 11 including providing means carried by said handle carrying illumination means for illuminating said zone.

13. The method of claim 1 including a bearing on said support for supporting said sheath to be rotated relative to the support.

14. The method of claim 13 including providing a double O-ring seal associated with said bearing for engaging said bearing during sheath rotation.

15. In apparatus for treating body tissue, the combination comprising
   a) a support providing a viewing channel, and an elongated optical stem, associated with said channel, and defining an axis, which extends forwardly,
   b) a sheath received on said stem and supported for controlled rotation about said axis and into a selected angular position relative to said support, to gain access to a selected body tissue zone to be treated,
   c) means carried on the sheath to be rotated therewith, to eject flowable treatment material onto or into said tissue at said zone, d) said sheath being controllably rotatable to the selected angular position about said axis to enable controlled ejection of said treatment material at said selected zone, e) said means including a guide on and exposed externally of the sheath for removably and forwardly receiving a syringe needle for passing said treatment material adjacent a portion of said sheath offset from said axis, after rotation of the sheath to said selected angular position, said sheath having a forward end, said guide extending near said forward end, and angled relative to said axis.

16. The apparatus of claim 15 wherein said means includes guide on the sheath for removably receiving a syringe needle for passing said treatment material adjacent a portion of said sheath offset from said axis, after rotation of the sheath to said selected angular position.

17. The apparatus of claim 15 including means on the sheath and on said support to provide indications of the extent of said rotating of said sheath, visible via said viewing channel.

18. The apparatus of claim 15 including means connected to the support to pass auxiliary fluid into the stem for infusion at a treatment zone.

19. The apparatus of claim 16 including said syringe having its needle reasonably supported by said guide, which is tubular.

20. The apparatus of claim 15 including fiber optics illumination means extending about the stem and within the rotatable sheath, to illuminate said zone.

* * * * *